US008003820B2

(12) United States Patent
Mandava et al.

(10) Patent No.: US 8,003,820 B2
(45) Date of Patent: Aug. 23, 2011

(54) PROCESS FOR PREPARING BISPHOSPHONIC ACIDS

(75) Inventors: Venkata Naga Brahmeswara Rao Mandava, Hyderabad (IN); Radha Krishna Singam Setty, Hyderabad (IN); Nagaraju Manne, Nalgonda (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 930 days.

(21) Appl. No.: 11/550,430

(22) Filed: Oct. 18, 2006

(65) Prior Publication Data

US 2007/0142636 A1 Jun. 21, 2007

Related U.S. Application Data

(60) Provisional application No. 60/745,675, filed on Apr. 26, 2006, provisional application No. 60/805,680, filed on Jun. 23, 2006.

(30) Foreign Application Priority Data

Oct. 20, 2005 (IN) .......................... 1514/CHE/2005
Mar. 7, 2006 (IN) ............................ 391/CHE/2006

(51) Int. Cl.
*C07F 9/22* (2006.01)

(52) U.S. Cl. ............... 562/13; 562/12; 548/112; 546/22
(58) Field of Classification Search .................... 562/13, 562/12; 546/22; 548/112
See application file for complete search history.

(56) References Cited

U.S. PATENT DOCUMENTS

| 4,407,761 A | 10/1983 | Blum et al. |
| 4,705,651 A | 11/1987 | Staibano |
| 4,922,007 A | 5/1990 | Kieczykowski et al. |
| 5,019,651 A | 5/1991 | Kieczykowski |
| 5,908,959 A | 6/1999 | Kubela et al. |
| 6,281,381 B1 | 8/2001 | Finkelstein et al. |
| 6,573,401 B1 | 6/2003 | Bosch i Liado et al. |
| 7,038,083 B2 * | 5/2006 | Lidor-Hadas et al. .......... 564/15 |
| 2003/0013918 A1 | 1/2003 | Cowan et al. |
| 2004/0043967 A1 | 3/2004 | Lidor-Hadas et al. |
| 2007/0173645 A1 * | 7/2007 | Danda et al. .................... 546/22 |

FOREIGN PATENT DOCUMENTS

| WO | 95/06052 A1 | 3/1995 |
| WO | 98/34940 A1 | 8/1998 |
| WO | 02/090367 A1 | 11/2002 |
| WO | 03/097655 A1 | 11/2003 |
| WO | 2005/044831 A2 | 5/2005 |

* cited by examiner

*Primary Examiner* — Rei-tsang Shiao
(74) *Attorney, Agent, or Firm* — Robert A. Franks; Thomas C. McKenzie; Balaram Gupta

(57) ABSTRACT

A process for preparing a bisphosphonate compound comprises reacting a carboxylic acid with a phosphonating agent, in a cresol solvent.

17 Claims, 1 Drawing Sheet

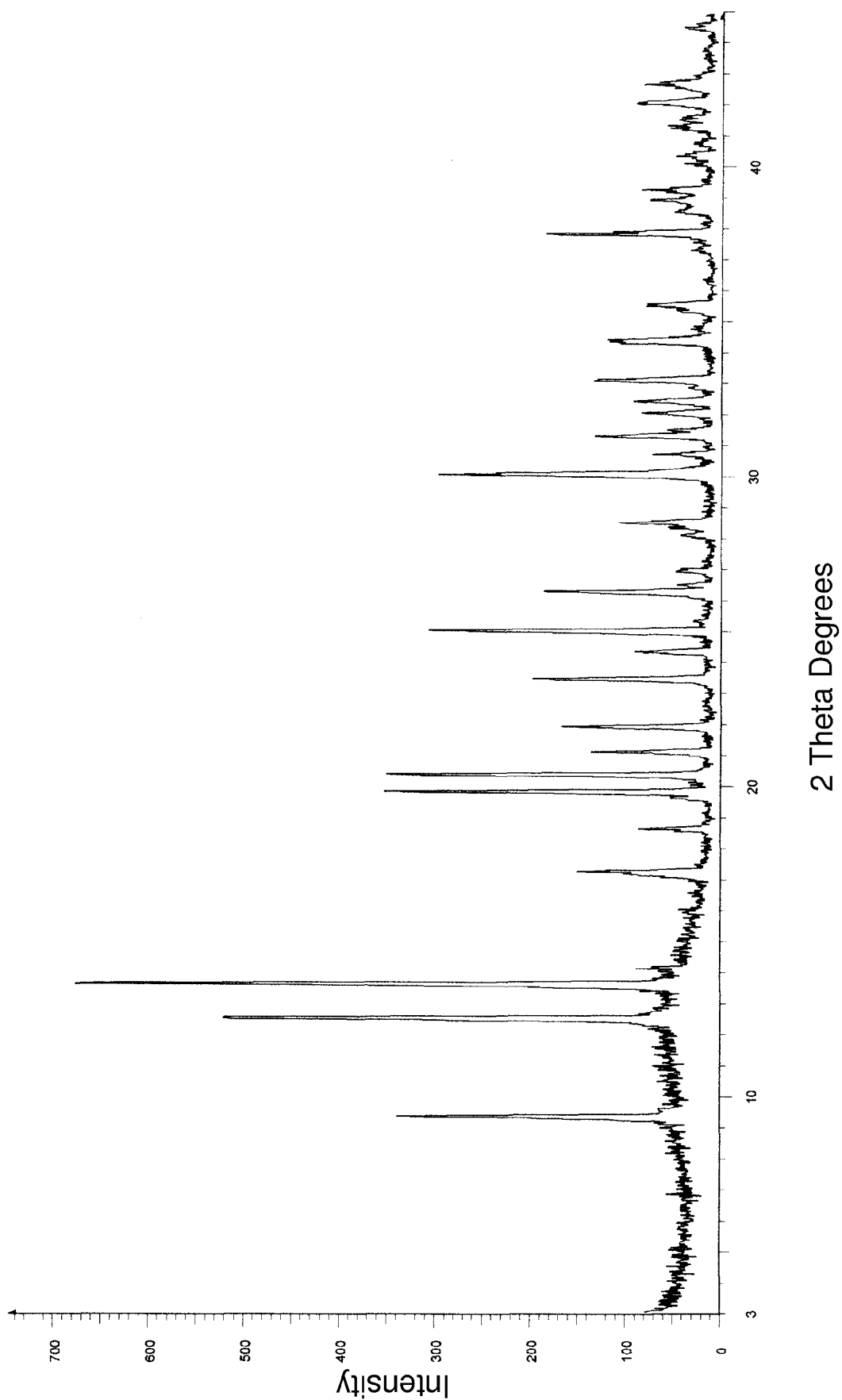

PROCESS FOR PREPARING BISPHOSPHONIC ACIDS

INTRODUCTION TO THE INVENTION

The present invention relates to a process for the preparation of bisphosphonic acids, represented by the compound of Formula I, or salts thereof. More specifically the present invention relates to a process for preparation of compound of Formula I or a salt thereof by reaction of a carboxylic acid compound of Formula II (the X and Y substituents being described later), or a salt thereof, with a phosphonating agent in a cresol diluent.

Formula I $$\text{Y}-\text{X}-\underset{\underset{\text{O}=\overset{|}{\text{P}}-\text{OH}}{|}}{\overset{\overset{\text{O}=\overset{|}{\text{P}}-\text{OH}}{|}}{\text{C}}}-\text{OH}$$
(with OH groups on each P)

Formula II $$\text{Y}-\text{X}-\underset{\text{O}}{\overset{\text{O}}{\parallel}}-\text{OH}$$

The present invention particularly relates to a process for the preparation of bisphosphonic acid compounds of Formula III to Formula X, respectively being named alendronic acid, pamidronic acid, risedronic acid, zoledronic acid, ibandronic acid, minodronic acid, neridronic acid and olpadronic acid, or salts thereof.

Formula III $$\text{H}_2\text{N}-(\text{CH}_2)_3-\text{C}(\text{P(O)(OH)}_2)_2-\text{OH}$$

Formula IV $$\text{H}_2\text{N}-(\text{CH}_2)_2-\text{C}(\text{P(O)(OH)}_2)_2-\text{OH}$$

Formula V (pyridyl)-$\text{CH}_2-\text{C}(\text{P(O)(OH)}_2)_2-\text{OH}$

Formula VI (imidazolyl)-$\text{N}-\text{CH}_2-\text{C}(\text{P(O)(OH)}_2)_2-\text{OH}$ Formula VII $$\text{H}_3\text{C}-(\text{CH}_2)_4-\underset{\text{H}_3\text{C}}{\text{N}}-(\text{CH}_2)_2-\text{C}(\text{P(O)(OH)}_2)_2-\text{OH}$$

Formula VIII (imidazo[1,2-a]pyridyl)-$\text{CH}_2-\text{C}(\text{P(O)(OH)}_2)_2-\text{OH}$ Formula IX $$\text{H}_2\text{N}-(\text{CH}_2)_5-\text{C}(\text{P(O)(OH)}_2)_2-\text{OH}$$

Formula X $$\text{H}_3\text{C}-\underset{\text{H}_3\text{C}}{\text{N}}-(\text{CH}_2)_2-\text{C}(\text{P(O)(OH)}_2)_2-\text{OH}$$

Bisphosphonate compounds have generally been prepared by the reaction of carbonyl compounds with phosphorous halides. Different processes using a variety of diluents have been reported in the literature for preparation of bisphosphonates. However they have some disadvantages associated with their use.

U.S. Pat. No. 4,705,651 discloses a process for preparing diphosphonic acids by reacting a particular molar ratio 1:1.25:2 of carboxylic acid to orthophosphorous acid to phosphorous trihalide, in the absence of solvents/diluents, then pouring the molten reaction product into a $C_1$-$C_3$ alcohol.

U.S. Pat. No. 4,407,761 discloses a process for the preparation of ω-amino-1-hydroxylalkylidine-1,1-bisphosphonic acids. The process comprises reaction of carboxylic acid with phosphorus acid and phosphorus trichloride using chlorobenzene as the diluent, leading to the formation of a sticky, orange pyrophoric solid.

U.S. Pat. Nos. 4,922,007 and 5,019,651 describe the process for the preparation of 4-amino-1-hydroxybutylidene or its salts thereof using methane sulphonic acid as a diluent. The reaction between methane sulfonic acid and phosphorous trichloride is highly exothermic.

U.S. Pat. No. 5,908,959 and International Application Publication Number WO 98/34940 disclose the use of long polyalkylenes (glycols) as diluents to prevent the solidification of the reaction mixture in the preparation of alendronate sodium. However, the solidification cannot be totally avoided and the glycols cannot be recycled as they are converted to their corresponding chloride derivatives.

International Application Publication Number WO 02/090367 discloses the use of aryl alkyl or alkyl ethoxylates or triglycerides such as plant or animal oils for solubilizing the reaction mixture in the preparation of alendronate sodium U.S. Patent Application Publication No. 2004/0043967 A1 discloses the use of aromatic hydrocarbons or silicone fluids as diluents for the preparation of biphosphonic acids.

International Application Publication Number WO 05/044831 describes the use of a water miscible neutral solvent such as sulfolane as a diluent for preparation of biphosphonic acids.

U.S. Pat. No. 6,573,401 discloses the preparation of 4-amino-1-hydroxybutylidene-1,1-bisphosphonic acid and of the trihydrated monosodium salt thereof, comprising of reacting 4-aminobutyric acid with a phosphonation mixture formed by phosphorous acid and methanesulfonic anhydride and thereafter hydrolyzing the product of said reaction and isolating the products by adjustment of the pH.

International Application Publication Number WO 95/06052 discloses a process for the purification of the alendroante sodium, the process comprising heating the crude alendronate sodium in de-ionized water at 50° C., filtering, atmospherically distilling followed by cooling to room temperature and finally cooling the slurry for two hours then filtering with vacuum. The process requires a long time for the completion of the reaction, which is not desirable at an industrial scale.

International Application Publication No. WO 2003/097655 describes the process for the preparation of bisphosphonic acids, which comprises reaction of a carboxylic acid with a phosphonating agent using an aromatic hydrocarbon as a diluent, especially toluene.

The present invention provides a process wherein a water miscible neutral diluent such as cresol is used for preparation of bisphosphonic acid compounds, making the process safe and convenient.

The process of the present invention is suitable for industrial scale up and can be used commercially. Since cresol is water miscible, the reaction mixture can be conveniently worked up by quenching into water, the intermediates subsequently being hydrolyzed and the final bisphosphonic acid product directly isolated from the reaction mixture, if desired in the form of a salt thereof.

SUMMARY OF THE INVENTION

The present invention relates to a process for preparation of bisphosphonic acids, represented by the compound of Formula I or salts thereof.

In one aspect the present invention provides a process for preparation of a bisphosphonic acid compound of Formula I or a salt thereof

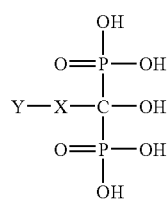

Formula I wherein:

X is a straight chain alkyl, a branched alkyl, or a cyclic alkyl chain having 1 to about 10 carbon atoms, which can optionally contain 1 to 3 nitrogen, oxygen, or sulfur atoms in the chain; and Y is an alkyl, aralkyl, aromatic or hetero aromatic group, which can be optionally substituted by a group having the formula

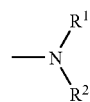

wherein $R^1$ and $R^2$ are independently hydrogen or straight chain, branched, or cyclic alkyl groups, each independently having 1 to about 10 carbon atoms; which process comprises reacting a carboxylic acid compound of Formula II or a salt thereof

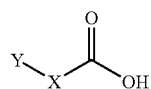

Formula II wherein X, Y are as described above, with a phosphonating agent in a cresol diluent.

In a first embodiment, the present invention provides a process comprising reacting 4-aminobutyric acid with phosphonating agent in a cresol diluent to prepare alendronic acid.

In a second embodiment, the present invention provides a process comprising reacting 3-aminopropionic acid with phosphonating agent in a cresol diluent to prepare pamidronic acid.

In a third embodiment, the present invention provides a process comprising reacting 3-pyridylacetic acid with phosphonating agent in a cresol diluent to prepare risedronic acid.

In a fourth embodiment, the present invention provides a process comprising reacting 1-imidazolylacetic acid with phosphonating agent in a cresol diluent to prepare zoledronic acid.

In a fifth embodiment, the present invention provides a process comprising reacting N-(n-pentyl)-N-methyl-3-aminopropionic acid with phosphonating agent in a cresol diluent to prepare ibandronic acid.

In a sixth embodiment, the present invention provides a process comprising reacting 2-(imidazo[1,2-a]pyridin-2-yl) ethanoic acid with phosphonating agent in a cresol diluent to prepare minodronic acid.

In a seventh embodiment, the present invention provides a process comprising reacting 6-aminohexanoic acid with phosphonating agent in a cresol diluent to prepare neridronic acid.

In an eighth embodiment, the present invention provides a process comprising reacting 3-(dimethylamino) propionic acid with phosphonating agent in a cresol diluent to prepare olpadronic acid.

In another aspect the present invention provides a process for the purification of bisphosphonate salts comprising crystallizing the salts from a mixture of a ketone and water.

In a related embodiment, the present invention provides a process for the purification of alendronate sodium comprising crystallizing from a mixture of ketone and water.

BRIEF DESCRIPTION OF THE DRAWING

FIG. 1 is an X-ray powder diffraction ("XRPD") pattern of alendronate sodium trihydrate prepared according to Example 2.

DETAILED DESCRIPTION OF THE INVENTION

The present invention relates to a process for preparation of bisphosphonic acids represented by the compound of Formula I, or a salt thereof.

A process for preparation of bisphosphonic acid having Formula I, or a salt thereof,

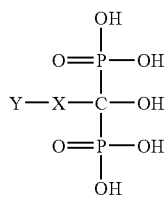

Formula I wherein:

X is a straight chain alkyl, a branched alkyl or a cyclic alkyl chain with 1 to about 10 carbon atoms, which can optionally contain hetero atoms; and Y is an alkyl, aralkyl, aromatic or hetero aromatic group, which can be optionally substituted by a group having the formula

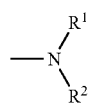

wherein, $R^1$ and $R^2$ independently are hydrogen or a straight chain, branched or cyclic alkyl groups, each independently having 1 to about 10 carbon atoms; comprises reacting a carboxylic acid compound of Formula II or a salt thereof

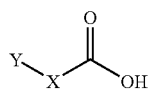

Formula II wherein X and Y are as described above,
with a phosphonating agent in a cresol diluent.

The bisphosphonic acids can be obtained in a safe manner with high yield and purity when using the process of the present invention. The present invention uses a cresol as a diluent, which is a relatively safe and inexpensive water miscible diluent for preparation of bisphosphonic acids.

Suitable carboxylic acids that can be used in the present invention include but are not limited to 4-aminobutyric acid, 3-aminopropionic acid, 3-pyridylacetic acid, 1-imidazolylacetic acid, N-(n-pentyl)-N-methyl-3-aminopropionic acid, 2-(imidazo[1,2-a]pyridin-2-yl) ethanoic acid, 3-(dimethylamino) propionic acid and the like.

Suitable cresol diluents that can be used in the present invention include but are not limited to p-cresol, o-cresol, m-cresol, tricresol, dicresol and the like.

Suitable phosphonating agents that can be used in the present invention include but are not limited to phosphorous acid in combination with phosphorous trichloride, phosphorous pentachloride, phosphorous pentachloride, phosphorous tribromide, phosphorous pentabromide, phosphorous oxybromide, and the like.

Suitable temperatures for conducting the reaction range from about −10° C. to about 150° C., or from about 0° C. to 100° C. The duration of maintenance of the reaction mixture at the reaction temperatures for reaction completion vary considerably depending on the reactants and conditions chosen, for example about 1 to 48 hours, or about 1 to 36 hours, or about 5 to 24 hours.

The reaction mass obtained after the completion of the reaction may optionally be filtered, or the reaction mass may be directly used in the next stage.

If it is desired to isolate the bisphosphonic acid as a salt thereof, the obtained bisphosphonic acid is treated with a base followed by precipitating the obtained salt and the precipitated salt may be isolated by any separation methods known in the art, such as centrifugation, gravity filtration or vacuum filtration.

Suitable salts are obtained by reacting the acid with bases such as lithium, sodium, potassium and the like. The isolation of the salt can be carried out by using conventional techniques.

The obtained salt can be dried by using any technique, such as fluid bed drying (FBD), spin flash drying, aerial drying, oven drying or other techniques known in the art at temperatures of about 20° C. to 60° C. or from 30° C. to 40° C. with or without application of vacuum and/or under inert conditions.

In one embodiment the present invention provides a process for the preparation of 4-amino-1-hydroxybutylidene-1,1-bisphosphonic acid monosodium trihydrate (alendronate sodium trihydrate) of Formula IIIa,

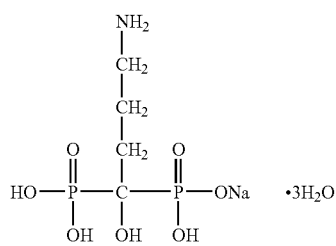

Formula IIIa comprising the steps of:

a) reacting 4-aminobutyric acid with a phosphonating agent in the presence of cresol as diluent;

b) adding water to the reaction mixture of step b);

c) reacting with base to form a corresponding sodium salt; and d) recovering the alendronate sodium trihydrate from the reaction mixture.

Suitable phosphonating agents that can be used in step a) include but are not limited to phosphorous acid in combination with phosphorous trichloride, phosphorous pentachloride, phosphorous tribromide, phosphorous pentabromide, phosphorous oxybromide, and the like.

The 4-aminobutyric acid that is used in step a) can also be used in the form of an acid addition salt, which includes but is not limited to the hydrochloride salt, hydrobromide salt and the like.

The cresols that can be used in step a) include but are not limited to o-cresol, m-cresol, p-cresol, tricresol, dicresol and the like;

Suitable temperatures for conducting the reaction can range from about 10° C. to about 80° C., or from about 30° C. to 70° C., or from about 40° C. to 60° C. Suitably, the reaction will be maintained at the reaction temperatures at least until the reaction is complete, this time varying depending on the particular reactants and conditions chosen and frequently can be from about 1 to 10 hours, or from about 1 to 8 hours. The reaction mass obtained after the completion may be directly used in the next stage.

Step b) involves addition of water to quench the reaction mixture.

Water added to the reaction mixture for quenching is also used for hydrolyzing the reaction mass.

Water quantities that can be used in the reaction may range from about 2 times to about 8 times the weight of the 4-aminobutyric acid used in the reaction.

Suitably quenching can be done by adding water to the reaction mass or by adding the reaction mass to the water. In one embodiment of the invention, the reaction mass is added to the water to better control temperature rise due to the exothermic reaction while quenching.

After quenching, the aqueous layer is separated from the organic layer and the aqueous layer is subjected to heating.

The aqueous material can be heated to a suitable temperature so that a phosphonate ester formed in the step a) is converted to its corresponding acid.

Suitable temperatures for heating the reaction mixture may range from about 80° C. to about 110° C., or from about 90° C. to 100° C. The reaction mixture can be maintained at the reaction temperatures at least until the conversion is complete, frequently for about 1 to 20 hours, or about 4 to 6 hours.

Step c) involves reacting with a base to form alendronate monosodium trihydrate.

Suitable bases that can be used for the conversion of the bisphosphonic acid into its salt include but are not limited to alkali metal compounds such as sodium hydroxide, sodium carbonate, sodium bicarbonate and the like, and the corresponding potassium compounds. These bases can be used in the form of solids or in the form of aqueous or alcoholic solutions.

In preferred embodiment sodium hydroxide is used as the base in the form of an aqueous solution and the concentration of the said solution may vary from about 20 to 60% by weight.

The amount of base that is required for the reaction is determined by measuring the pH of the reaction mixture. Suitably for preparing a monosodium salt, reaction mixture pH can be adjusted to about 3.5 to 5.5, or about 4 to 4.5, by the base addition.

Step d) involves recovering alendronate monosodium trihydrate from the reaction mixture.

Recovery involves either saturating the solution to precipitate the solid or cooling the solution to lower temperatures or concentrating the solution followed by isolation.

Suitable solvents which can be added to an aqueous solution of bisphosphonate to achieve saturation include but are not limited to alcoholic solvents such as methanol, ethanol, propanol and the like.

The solid precipitate is isolated by using conventional techniques such as centrifugation, gravity filtration, and vacuum filtration and like.

The obtained solid material is further dried using any technique such as fluid bed drying (FBD), spin flash drying, aerial drying, oven drying or other techniques known in the art at temperatures of about 40° C. to 75° C. with or without application of vacuum and/or under inert conditions. In an embodiment drying is carried out under vacuum at about 65° C.

In another embodiment when 3-aminopropionic acid is used as a starting material, the product obtained is pamidronic acid.

In a further embodiment when 3-pyridylacetic acid of Formula Xi is used as a starting material, the product obtained is risedronic acid.

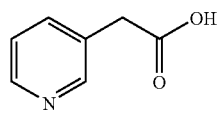

Formula XI

In an embodiment when 1-imidazolyl acetic acid of Formula XII is used as a starting material, the product obtained is zoledronic acid.

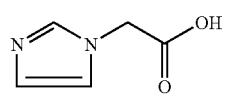

Formula XII

In the embodiment when N-(n-pentyl)-N-methyl-3-aminopropionic acid is used as a starting material, the product obtained is ibandronic acid.

In an embodiment when 2-(imidazo[1,2-a]pyridin-2-yl) ethanoic acid is used as a starting material, the product obtained is minodronic acid.

In another embodiment when 6-aminohexanoic acid is used as a starting material, the product obtained is neridronic acid.

In the embodiment when 3-(dimethylamino) propionic acid is used as a starting material, the product obtained is olpadronic acid.

In another aspect the present invention provides a process for the purification of bisphosphonates.

A process for the purification of bisphosphonates comprises crystallizing the bisphosphonate from a mixture of a ketone and water.

Suitable ketones that can be used for the purification include but are not limited to acetone, methyl ethyl ketone, methyl isobutyl ketone, methyl isopropyl ketone, isopropyl ketone, propanone, 2-butanone and the like.

In another embodiment the present invention provides a process for purification of alendronate sodium trihydrate by crystallizing from a mixture of a ketone and water comprising the steps of:
i) providing a solution of crude alendronate sodium in a suitable solvent;
ii) cooling the solution of step i) to precipitate the solid; and
iii) recovering the alendronate sodium trihydrate.

The step of providing a solution of alendroante sodium may include dissolving any form of alendronate sodium in a suitable solvent or obtaining an existing solution from a previous processing step, such as a synthesis of alendronate sodium.

Suitable solvents that can be used for providing a solution include any solvent or mixture of solvents in which the required components are soluble. Examples of such solvents include but are not limited to: protic solvents such as water; alcohols such as methanol, ethanol, n-propanol, isopropanol, n-butanol, isobutanol, t-butanol and the like; ketones such as acetone, methyl ethyl ketone, methyl isobutyl ketone, methyl isopropyl ketone, isopropyl ketone, propanone, 2-butanone and the like; and mixtures thereof In an embodiment a mixture of water and methyl ethyl ketone (MEK) is used for providing a solution of alendronate sodium.

The ratio of water to ketone in the mixture can be varied from about 4:1 to about 1:5 by volume and the dissolution temperature may range from about 10 to 80° C., or about 20° C. to 75° C., or at room temperature.

The concentration of the solution of alendronate sodium in step i) will typically be high for improved process efficiency, such as about 20% to 45% by w/v. Lower concentrations can be used, but with decreased yields.

The solution is cooled in step (ii) to lower temperatures to induce crystallization, such as about −5° C. to 10° C., or 0° C. to 5° C. Other temperatures can be used, but may result in a decreased yield.

The isolation techniques that are employed in step (iii) to recover the solid formed include conventional techniques such as centrifugation, gravity filtration and the like, either by applying or without applying vacuum and/or under inert conditions.

The solid product that is obtained can optionally be dried in order to bring the residual solvent contents within commercially acceptable limits or to render the product substantially free of residual solvents.

Drying can be carried out under reduced pressure until the residual solvent content reduces to an amount that is within the limits given by the International Conference on Harmonisation of Technical Requirements for Registration of Pharmaceuticals for Human Use ("ICH") guidelines. The guideline solvent level depends on the type of solvent but is not more than about 5000 ppm, or about 4000 ppm, or about 3000 ppm.

The drying can be carried out at any desired reduced pressures, such as below about 200 mm Hg or below about 50 mm Hg, at temperatures such as about 25° C. to about 50° C. The drying can be carried out for any desired time period that achieves the desired result, such as times about 1 to 20 hours. Drying may also be carried out for shorter or longer periods of time depending on the product specifications and drying conditions.

Drying can be suitably carried out in a tray dryer, vacuum oven, air oven, or using a fluidized bed drier, spin flash dryer, flash dryer and the like or other techniques known in the art.

Alendronate sodium trihydrate prepared according to the process of the invention is characterized by its XRPD pattern having prominent peaks approximately at about 9.2, 12.4, 13.4, 19.7, 20.2, 24.9, and 26.1, ±0.2 degrees 2θ, using Cu Kα-1 radiation.

Alendronate sodium trihydrate prepared according to the process of present invention typically contains about 16 to 17% of water by weight upon drying at 140° C. under a vacuum of 5 mm Hg.

Alendronate sodium trihydrate prepared according to present invention contains less than or equal to 0.1% by weight of 4-aminobutryic acid of Formula XIII;

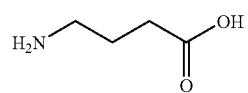

Formula XIII and less than or equal to about 0.1% by weight of (3-amino-1-phosphono-1-p-tolyloxy propyl)-phosphonic acid impurity ("macromer impurity") of Formula XIV

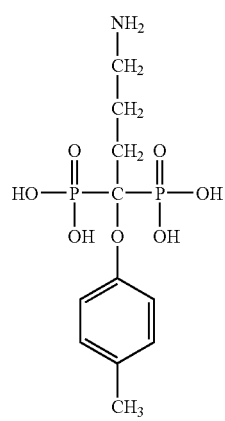

Formula XIV as determined by high performance liquid chromatography ("HPLC").

Alendronate sodium trihydrate obtained by the process of the invention is analyzed using the HPLC method described in *United States Pharmacopeia* 29, United States Pharmacopeial Convention, Inc., Rockville, Md., 2006, at pages 71 and 72, and compounds of Formula XIII and Formula XIV are observed at the following retention times ("RT").

| Compound | RT | RRT |
| --- | --- | --- |
| Alendronate sodium | 5.54 | 1.0 |
| 4-aminobutyric acid | 10.44 | 1.88 |
| Macromer impurity | 10.88 | 1.96 |

The 4-aminobutyric acid impurity limit of detection is 0.0045%, and the limit of quantitation is 0.019% by weight in alendronate sodium.

The term "RRT" is used herein to indicate the relative retention time of the particular impurity against pure alendronate sodium standard (assigned an RRT value of 1.0) during an HPLC analysis. A relative standard deviation that is equal to or less than 5% for a population of 6 injections is acceptable while referring to RRT values.

Alendronate sodium trihydrate obtained by the process of the present invention contains less than about 5000 ppm, or less than about 3000 ppm, or less than about 1000 ppm, of total residual organic solvents and less than about 200 ppm, or less than about 100 ppm, or less than about 50 ppm, of individual residual organic solvents as determined by gas chromatography.

In still another aspect, the present invention provides alendronate sodium hydrochloride having particle sizes less than about 450 μm.

The $D_{10}$, $D_{50}$, and $D_{90}$ values are useful ways for indicating a particle size distribution. $D_{90}$ refers to the value for the particle size for which at least 90 volume percent of the particles have a size smaller than the value. Likewise $D_{50}$ and $D_{10}$ refer to the values for the particle size for which 50 volume percent, and 10 volume percent, of the particles have a size smaller than the value. Methods for determining $D_{10}$, $D_{50}$ and $D_{90}$ include laser diffraction, such as using Malvern Instruments Ltd. (of Malvern, Worcestershire, United Kingdom) equipment.

In another aspect of the present invention, there is provided alendronate sodium having a particle size distribution pattern of $D_{10}$ less than or equal to about 160 μm, $D_{50}$ less than or equal to about 250 μm, and D90 less than or equal to about 420 μm. There is no specific lower limit for any of the D values.

In another aspect of the present invention there is provided alendronate sodium having a surface area of about 0.06 to 0.15 m²/g.

In another aspect of the present invention, there is provided alendronate sodium having high purity, which is well suited for use in pharmaceutical compositions, as well as a related method of treatment.

The present invention is eco-friendly, industrially well suited, commercially viable, reproducible and cost effective.

These and other specific aspects and embodiments of this invention are described in further detail by the examples below, which examples are not intended to limit the scope of the appended claims in any manner.

Example 1

Preparation of Alendronate Sodium Trihydrate 100 g of 4-aminobutyric acid and 400 ml of p-cresol were taken in a clean and dry round bottom flask followed by stirring for about 15 minutes. To the resultant solution 120 g of phosphorous acid was added and the mixture subjected to heating to a temperature of about 42° C. with simultaneous stirring. 270 ml of phosphorous trichloride was slowly added to the above reaction mixture at about 62° C. over about 45 minutes. The resultant suspension was heated to about 75° C. for about 5 hours followed by cooling to about 27° C. 400 ml of water was added to the with simultaneous stirring followed by separating the aqueous layer from the organic layer. 400 ml of water was added to the aqueous layer and subjected to stirring followed by separating the aqueous layer. The aqueous layer was heated to a temperature of about 103° C. with simultaneous stirring. The pH of the mass was adjusted to about 4.6 by the addition of a mixture of 412 ml of 50% aqueous sodium hydroxide solution followed by stirring at about 22° C. for about 3 hours and cooling to 5° C. The obtained solid was filtered under vacuum followed by washing with 250 ml of chilled water and drying at a temperature of about 65° C. under vacuum to afford 155.0 g (49.2%) of alendronate sodium trihydrate.

Purity by HPLC: 97.04%.
4-aminobutyric acid impurity: 0.38%
Macromer impurity: 2.58%.

Example 2

Purification of Alendronate Sodium Trihydrate.

A clear solution was prepared by dissolving 20 g of crude alendronate sodium in a solvent mixture containing 400 ml of water and 100 ml of methyl ethyl ketone by heating to reflux at temperature of about 72° C. with simultaneous stirring over a period of about 70 minutes. The solution was than filtered through cloth to make it free from particles, the filter was washed with 8 ml of water and the filtrate was transferred into another round bottom flask, subjected to cooling to a temperature of about 30° C. and than to 5° C. with simultaneous stirring for a period of about 90 minutes until the solid separated. The solid that was obtained was separated through filtration followed by washing with a mixture of 2 ml of methyl ethyl ketone and 4 ml of water and subjected to suction drying at a temperature of about 25° C. for a period of about 20 minutes. Then the obtained wet solid was finally subjected to drying in an oven by applying vacuum at about 100 milli-bar to afford 17 g (yield 85%) alendronate sodium trihydrate.

Purity of alendronate sodium: 99.86% by HPLC.
Loss on drying: 16.62% w/w.
4-aminobutryic acid impurity: Not detected
Macromer impurity: 0.06% by HPLC.

Example 3

Preparation of Alendronate Sodium Trihydrate 80 liters of p-cresol was taken into a reactor followed by the addition of 20 kg of 4-aminobutyric acid and 24 kg of phosphorous acid, and the mass was subjected to heating to a temperature of about 62.5° C. for a period of about 1.5 hours. 54 liters of phosphorous trichloride was added to the above reaction mass and subjected to heating to a temperature of about 73.6 for a period of about 6 hours. 140 liters of water was taken into another reactor and cooled to a temperature of about 13° C. followed by the addition of the above obtained reaction mass and subjected to stirring for a period about 30 minutes. The thus obtained mass was subjected to heating at a temperature of about 43.4° C. for a period of about 15 minutes and allowed to settle for a period of about 45 minutes. The aqueous layer was separated and subjected to heating to reflux at 98.9° C. for a period of about 5 hours, followed by cooling to a temperature of about 44.5° C. over a period of about 30 minutes with simultaneous stirring. The reaction mass was allowed to settle for a period of about 45 minutes and the aqueous layer was separated. 90 liters of aqueous sodium hydroxide solution was slowly added to the aqueous layer to produce a pH of 4.33. The reaction mass was subjected to stirring for a period of about 45 minutes followed by cooling to a temperature of about 2° C. over a period of about 8 hours. Finally, the obtained solid material was subjected to centrifugation followed by washing with precooled water and then subjected to centrifugation to afford 34.8 kg of alendronate sodium trihydrate.

Purity by HPLC: 99.62 weight %.
4-amino butyric acid: Not detected.
Macromer impurity: 0.37 weight %.
Loss on drying: 17.12% w/w.

Example 4

Purification of Alendronate Sodium Trihydrate 324 liters of water was taken into a reactor followed by the addition of 18 kg of crude alendronate sodium obtained from Example 3 and subjected to heating at a temperature of about 73.7° C. Thus the obtained mass was transferred into another reactor followed by the addition of 36 liters of water and subjected to cooling to a temperature of about 20° C. 180 liters of methyl ethyl ketone was added to the mass and subjected to cooling to a temperature of about 2.3° C. over a period of about 2 hours. The obtained solid mass was subjected to centrifugation followed by washing with 9 liters of a 1:1 mixture by volume of methyl ethyl ketone and water and subjected to spin-drying. Finally the obtained purified alendronate sodium was subjected to drying at a temperature of about 78° C. followed by sifting through a 40 mesh sieve to afford 16.1 g (89.4%) of alendronate sodium trihydrate.

Purity by HPLC: 99.7 weight %
4-amino butyric acid: Not detected.
Macromer impurity: 0.02 weight %.
Residual Solvents by GC: ethanol 1 ppm and methyl ethyl ketone 20 ppm.
Heavy Metals: less than 10 ppm.
Loss on drying: 16.86% w/w.

Example 5

Preparation of Alendronate Sodium Trihydrate Using Triethylphosphate as a Diluent 10 g of 4-aminobutyric acid and 100 ml of triethylphosphate were charged in a clean and dry round bottom flask followed by stirring for about 15 minutes. 11.94 g of phosphorous acid was charged followed by addition of 27 ml of phosphorous trichloride at about 29° C. over about 2 hours. The resultant suspension was heated to about 60° C. for about 6 hours followed by cooling to about 29° C. After the completion of the reaction, the reaction mass was quenched by the addition of 80 ml of water over about 45 minutes. The resulting biphasic reaction mass was heated to about 110° C. for about 5 hours. The reaction mass was cooled to about 28° C. and the organic and aqueous layers were separated followed by cooling the aqueous layer to about 10° C. The pH of the resultant reaction mass was adjusted to about 4.3 by the addition of a mixture of 5.5 g of sodium hydroxide and 5 ml of 48% aqueous sodium hydroxide solution over about 45 minutes. The resulting reaction mixture was saturated by the addition of 30 ml of methanol over about 10-15 minutes followed by cooling to about 8° C. for about 45 minutes. The separated solid was filtered and the solid was washed with 10 ml of methanol followed by drying the solid obtained solid under vacuum at about 6° C. to afford 22 g of title compound with a purity by HPLC of 99.41%.

Example 6

Preparation of Alendronate Sodium Trihydrate Using Tricresyl Phosphate as a Diluent 50 ml of tricresyl phosphate and 5 g of 4-aminobutyric acid were charged in a clean and dry round bottom flask followed by stirring for about 15 minutes. To this mixture 5.97 g of phosphorous acid was charged and stirred for about 30 minutes. 13.52 ml of phosphorous trichloride was added over about 45 minutes at about 28° C. followed by heating to about 60° C. and stirred for about 6 hours. The resultant reaction suspension was heated to about –60° C. for about 5 hours followed by cooling to about 28° C. and the reaction mass was quenched by the addition of 40 ml of water over a period of 45 minutes. Organic and aqueous layers were separated and the aqueous layer was heated to about 100° C. for about 5 hours followed by cooling to about 10° C. The pH of the resultant reaction mass was adjusted to about 4.3 by the addition of a mixture of 13 g of sodium hydroxide and 3.5 ml of 48% aqueous sodium hydroxide solution over about 45 minutes. The resultant reaction mixture was saturated by charging of 150 ml of methanol followed by stirring for about 3 hours. The separated solid was filtered and the solid was washed with 15 ml of methanol followed by drying the solid at about 28° C. for about 45 minutes under vacuum to afford 4 g of title compound with a purity by HPLC of 99.72%.

Example 7

Preparation of Alendronate Sodium Trihydrate Using Trifluoromethane Sulphonic Acid as a Diluent 10 ml of trifluoromethane sulphonic acid was charged in a clean and dry round bottom flask followed by cooling to about 10° C. 10 g of 4-aminobutyric acid was charged in three lots over about 45 minutes followed by stirring for about 5-10 minutes. 11.94 g of phosphorous acid was charged and stirred for about 10-15 minutes followed by addition of 27 ml of phosphorous trichloride over about 45-60 minutes. The reaction suspension was heated to about 55° C. for about 18 hours followed by quenching the reaction by adding 80 ml of pre-cooled water slowly over a period of 45 minutes. The resultant reaction mass was heated to about 98° C. for about 4-5 hours followed by cooling to about 20° C. The pH of the reaction mass was adjusted to about 4.23 by the addition of a mixture of 10 g of sodium hydroxide and 7 ml of 48% aqueous sodium hydroxide solution over about 2 hours. The resultant reaction mass was cooled to about 10° C. for about 3 hours followed by filtering the separated solid and washing the solid with 25 ml of water. The solid obtained was dried at about 28° C. for about 20 minutes under vacuum to afford 21 g of title compound with purity by HPLC of 98.02%.

The invention claimed is:

1. A process for preparing a bisphosphonic acid having Formula I,

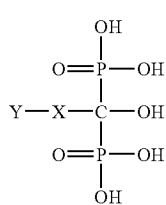

Formula I wherein:
X is a straight chain alkyl, a branched alkyl, or a cyclic alkyl chain having 1 to about 10 carbon atoms, which can optionally contain 1 to 3 nitrogen, oxygen, or sulfur atoms in the chain; and
Y is an alkyl, aralkyl, aromatic or hetero aromatic group, which can be optionally substituted by a group having a formula:

wherein $R^1$ and $R^2$ are independently hydrogen or straight chain, branched, or cyclic alkyl groups, each independently having 1 to about 10 carbon atoms;
or a salt thereof, comprising reacting a carboxylic acid with a phosphonating agent consisting essentially of a combination of phosphorous acid and at least one of phosphorous trichloride, phosphorous pentachloride, phosphorous pentachloride, phosphorous tribromide, phosphorous pentabromide, and phosphorous oxybromide, in a cresol solvent.

2. The process of claim 1, wherein a carboxylic acid is selected from the group consisting of at least one of 4-aminobutyric acid, 3-aminopropionic acid, 3-pyridylacetic acid, 1-imidazolylacetic acid, N-(n-pentyl)-N-methyl-3-aminopropionic acid, 2-(imidazo[1,2-a]pyridin-2-yl)ethanoic acid, and 3-(dimethylamino)propionic acid.

3. The process of claim 1, wherein a carboxylic acid is 4-aminobutyric acid.

4. The process of claim 1, wherein a phosphonating agent is a combination of phosphorous acid and phosphorous trichloride.

5. The process of claim 1, wherein a cresol is p-cresol.

6. The process of claim 1, further comprising reacting a bisphosphonic acid with a base to form a salt.

7. The process of claim 1, further comprising reacting a bisphosphonic acid with an alkali metal hydroxide to form a salt.

8. A process for preparing a bisphosphonic acid having Formula I,

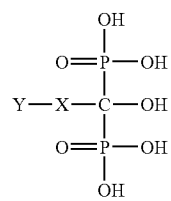

Formula I or a salt thereof, comprising reacting an acid having a formula:

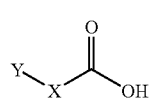

wherein:
X is a straight chain alkyl, a branched alkyl, or a cyclic alkyl chain having 1 to about 10 carbon atoms, which can optionally contain 1 to 3 nitrogen, oxygen, or sulfur atoms in the chain; and Y is an alkyl, aralkyl, aromatic or hetero aromatic group, which can be optionally substituted by a group having a formula:

wherein $R^1$ and $R^2$ are independently hydrogen or straight chain, branched, or cyclic alkyl groups, each independently having 1 to about 10 carbon atoms;
or a salt thereof, with a phosphonating agent consisting essentially of a combination of phosphorous acid and at least one of phosphorous trichloride, phosphorous pentachloride, phosphorous pentachloride, phosphorous tribromide, phosphorous pentabromide, and phosphorous oxybromide, in a cresol solvent.

9. The process of claim 8, wherein a carboxylic acid is selected from the group consisting of at least one of 4-aminobutyric acid, 3-aminopropionic acid, 3-pyridylacetic acid, 1-imidazolylacetic acid, N-(n-pentyl)-N-methyl-3-aminopropionic acid, 2-(imidazo[1,2-a]pyridin-2-yl)ethanoic acid, and 3-(dimethylamino)propionic acid.

10. The process of claim 8, wherein a carboxylic acid is 4-aminobutyric acid.

11. The process of claim 8, wherein a phosphonating agent is a combination of phosphorous acid and phosphorous trichloride.

12. The process of claim 8, wherein a cresol is p-cresol.

13. The process of claim 8, further comprising reacting a bisphosphonic acid with a base to form a salt.

14. The process of claim 8, further comprising reacting a bisphosphonic acid with an alkali metal hydroxide to form a salt.

15. The process of claim 8, further comprising the step of crystallizing the salt from a mixture of a ketone and water.

16. The process of claim 15, wherein the ketone is methyl ethyl ketone.

17. The process of claim 15, wherein the water and the ketone are in a ratio of about 4:1 to 1:1 by volume.

* * * * *